United States Patent [19]

Atkins et al.

[11] 4,451,681

[45] May 29, 1984

[54] METHODS OF PREPARING PENTANITROTOLUENE

[75] Inventors: Ronald L. Atkins; Richard A. Hollins; William P. Norris; Arnold T. Nielsen, all of Ridgecrest, Calif.; William S. Wilson, Greensborough, Australia

[73] Assignee: The United States of America as represented by the Secretary of the Navy, Washington, D.C.

[21] Appl. No.: 456,672

[22] Filed: Jan. 10, 1983

[51] Int. Cl.³ .............................................. C07C 79/10
[52] U.S. Cl. .................................................... 568/932
[58] Field of Search ....................... 564/441; 568/932; 149/105

[56] References Cited

U.S. PATENT DOCUMENTS

| | | | |
|---|---|---|---|
| 2,036,530 | 4/1936 | Knecht et al. | 260/124 |
| 3,087,972 | 4/1963 | Emmons et al. | 260/645 |
| 3,507,924 | 4/1970 | Hakansson et al. | 260/645 |
| 4,262,148 | 4/1981 | Nielsen et al. | 568/932 |

OTHER PUBLICATIONS

Nielsen et al., J. Org. Chem., 45, 2341 (1980).

*Primary Examiner*—Leland A. Sebastian
*Attorney, Agent, or Firm*—Robert F. Beers; W. Thom Skeer; Bruce H. Cottrell

[57] ABSTRACT

Pentanitrotoluene is prepared by a method which comprises preparing an aminodinitrotoluene from a precursor of either TNT or 2,5-dinitro-3-methylbenzoic acid, nitrating the aminodinitrotoluene to produce a nitramine intermediate, converting the nitramine intermediate to an aminotetranitrotoluene and oxidizing the aminotetranitrotoluene with peroxydisulfuric acid to pentanitrotoluene. Pentanitrotoluene is an explosive.

12 Claims, No Drawings

METHODS OF PREPARING PENTANITROTOLUENE

BACKGROUND OF THE INVENTION

This invention relates to methods of preparing an organic compound. More particularly, this invention relates to methods of preparing an organic compound having a plurality of nitro groups. Specifically, this invention relates to methods of preparing pentanitrotoluene.

DESCRIPTION OF THE PRIOR ART

Aromatic compounds with large numbers of nitro groups are well known to be explosives. Pentanitrotoluene is a known high energy explosive of considerable interest. Previously, pentanitrotoluene has been prepared in a multistep process involving as the last step the peroxydisulfuric acid oxidation of 3,5-bis(-diacetylamino)-2,4,6-trinitrotoluene, J. Org. Chem, 45, 2341 (1980). The overall yield of the process was low and limited the availability of pentanitrotoluene as an explosive. An improved method would use a readily available, inexpensive starting material, require a minimum of steps and give a higher yield. Accordingly, the authors of this specification have developed after a considerable amount of experimentation the hereinafter disclosed methods of preparing pentanitrotoluene.

SUMMARY OF THE INVENTION

According to this invention, pentanitrotoluene is prepared by the steps of: (a) preparing an aminodinitrotoluene from a starting material; (b) nitrating the aminodinitrotoluene to form a nitramine; (c) converting the nitramine to an aminotetranitrotoluene; and (d) oxidizing the aminotetranitrotoluene to produce pentanitrotoluene.

OBJECTS OF THE INVENTION

Therefore, it is an object of this invention to provide improved methods of preparing the explosive compound pentanitrotoluene.

It is another object of this invention to provide methods of preparing pentanitrotoluene in fewer overall steps from a commercially available starting material.

A further object of the present invention is to provide methods of preparing pentanitrotoluene with higher yields.

Other objects, advantages, and novel features of the present invention will become apparent from the following detailed description.

DESCRIPTION OF THE PREFERRED EMBODIMENT

Pentanitrotoluene may be prepared by carrying out the procedures set forth in the following specific examples.

EXAMPLE 1

50 grams of 2,4,6-trinitrotoluene was dissolved in 100 ml of p-dioxane. One ml of concentrated ammonium hydroxide solution was added giving a deep red solution. Hydrogen sulfide gas was bubbled into the stirred solution at a rate sufficient to maintain the temperature below 35° C. After one hour, $H_2S$ addition was stopped. Thin layer chromatography showed no starting material remaining. The precipitated sulfur was filtered off and the filtrate was poured into 500 ml of ice water. The resulting yellow solid was filtered and dried giving an essentially quantitative yield of a mixture of the desired 4-amino-2,6-dinitrotoluene (61%) and the partial reduction product 4-hydroxylamino-2,6-dinitrotoluene (39%) as determined by NMR spectroscopy.

Ten grams of this mixture was suspended in 500 ml of 3N HCl. 3.12 grams of potassium iodide was added, and the stirred solution was heated to reflux. After one hour an additional aliquot of KI was added. Following an additional half hour at reflux, the hot solution was filtered to give a clear red solution. The cooled solution was neutralized to pH 7.5 by addition of 140 ml of concentrated ammonium hydroxide solution. The precipatated yellow solid was filtered and dried. Recrystallization from methanol gave 4.2 g of the 4-amino-2,6-dinitrotoluene as yellow crystals (m.p. 168°–169° C.)

EXAMPLE 2

700 mg of 4-amino-2,3,5,6-tetranitrotoluene was dissolved in a mixture of 15 ml of 96% $H_2SO_4$ and 30 ml of 20% oleum. 3.5 ml of 98% $H_2O_2$ was added dropwise over about 20 minutes to the stirred solution and stirring was continued at room temperature overnight. Extraction and recrystallization from chloroform gave 633 mg of pentanitrotoluene as yellow crystals (m.p. 224°–235° C.); $^{13}C$ NMR ($CDCl_3$): 2.57 (S, 3, $CH_3$).

Anal. Calcd. for $C_7H_3N_5O_{10}$: C, 26.50; H, 0.95; N, 22.08. Found: C, 26.64; H, 0.92; N, 21.97.

The above is believed to be the best mode of practicing the invention by the inventors, however, the peroxydisulfuric acid oxidation of any of the three aminotetranitrotoluene isomers will yield the pentanitrotoluene. Alternative procedures for making the para isomer, 4-amino-2,3,5,6-tetranitrotoluene are set forth in the following examples.

EXAMPLE 3

1.7 grams of 4-amino-2,6-dinitrotoluene was dissolved in 10 ml of 96% $H_2SO_4$. 3.0 grams of paraformaldehyde was added in small portions over one hour to this stirred solution at 120° C. After heating at 120° C. for an additional hour the mixture was poured over ice and partially neutralized with about 75 ml of saturated $NaHCO_3$ solution. The mixture was extracted with 100 ml of methylene chloride and then dried over $MgSO_4$, filtered and evaporated to an orange solid. Crystallization from chloroform gave 690 mg of 4-amino-N-methyl-2,6-dinitrotoluene as orange crystals (m.p. 137°–139° C.).

EXAMPLE 4

200 mg of 4-amino-N-methyl-2,6-dinitrotoluene was dissolved in 8 ml of 96% $H_2SO_4$ and kept cool with an ice bath. 0.6 ml of 90% $HNO_3$ was added dropwise to the stirred solution and then the ice bath was removed. After stirring at room temperature for 3.5 hours, the mixture was extracted with four 10 ml portions of methylene chloride, dried over $MgSO_4$, filtered and evaporated. The residue was crystallized from chloroform to give 50 mg of the nitramine, 4-amino-N,2,3,5,6-pentanitrotoluene, as pale yellow crystals (m.p. 140°–170° C.). The nitramine was rapidly transformed into the 4-amino-2,3,5,6-tetranitrotoluene using a solution of anisole in $H_2SO_4$.

Nitration of the 4-amino-2,6-dinitrotoluene with a mixture of nitric and sulfuric acid, at room temperature resulted in a quantitative yield of the tetranitronitramine, 4-amino-N,2,3,5,6-pentanitrotoluene. A more preferable temperature of 10° C. or less can be used. Treatment of the nitramine with a solution of anisole in $H_2SO_4$ resulted in a 92% yield of the 4-amino-2,3,5,6-tetranitrotoluene.

EXAMPLE 5

600 mg of 4-amino-2,6-dinitrotoluene was dissolved in a mixture of 12 ml of glacial acetic acid and 36 ml of 96% $H_2SO_4$ and cooled in an ice bath. To this stirred solution, 1.8 ml of 90% $HNO_3$ in 12 ml of glacial acetic acid was slowly added dropwise. The mixture was stirred at 0° C. for 5 hours and then placed in a freezer overnight at 1°–10° C. The following morning the mixture was stirred for an additional 4 hours at 0° C. The mixture was extracted in four 50 ml portions of methylene chloride. The combined extracts were washed with two 100 ml portions of water, dried over $MgSO_4$ and evaporated at reduced pressure. This procedure yielded 680 mg of the nitramine, 4-amino-N,2,3,6-tetranitrotoluene as a pale yellow oil, which due to instability was used immediately without purification in the next step.

EXAMPLE 6

A solution of 680 mg of crude 4-amino-N,2,3,5-tetranitrotoluene was dissolved in 100 ml of 96% $H_2SO_4$ and cooled to 0° C. for about 2.5 days. The solution was then poured over 200–300 grams of ice and the resulting mixture extracted with two 150 ml portions of methylene chloride and then chloroform. The combined extracts were dried over $MgSO_4$ and evaporated to a yellow solid. Recrystallization from chloroform-hexane gave 310 mg of 4-amino-2,3,5,6-tetranitrotoluene. Oxidation as in Example 2 converted this to the pentanitrotoluene.

EXAMPLE 7

A mixture of 300 mg of 4-amino-2,6-dinitrotoluene and 480 mg of nitronium tetrafluoroborate in 50 ml of ethylene dichloride was stirred at room temperature for 2 hours. Then, 2 drops of water was added and stirring continued for another hour. The mixture was dried over anhydrous magnesium sulfate, filtered and evaporated to yield 243 mg of the nitramine, 4-amino-N,2,3,6-tetranitrotoluene as yellow crystals (m.p. 145°–185° C. -decomp.; IR peak at $2200^{-1}$ suggests a trace of diazo oxide). The nitramine is converted to the 4-amino-2,3,5,6-tetranitrotoluene as in Example 6.

The ortho isomer, 2-amino-3,4,5,6-tetranitrotoluene is prepared from trinitrotoluene as set forth in the following example.

EXAMPLE 8

1.0 gram of 2,4,6-trinitrotoluene was dissolved in 22 ml of glacial acetic acid. With vigorous stirring, 0.82 g of iron powder (400 mesh) was added in small portions over two hours. The red reaction suspension was diluted to 50 ml with water giving a bright yellow precipitate. Filtration gave 0.38 grams of 2-amino-4,6-dinitrotoluene of sufficient spectral and chromatographic purity for use in the subsequent synthesis without recrystallization.

The 2-amino-4,6-dinitrotoluene is subsequently converted either directly or through a nitramine intermediate to the ortho isomer of 2-amino-3,4,5,6-tetranitrotoluene. Oxidation as in Example 2 yields the pentanitrotoluene.

EXAMPLE 9

3.0 grams of 2-amino-4,6-dinitrotoluene was dissolved in 150 ml of 96% sulfuric acid at room temperature. 1.92 grams of 100% nitric acid was added dropwise with stirring, and the reaction mixture was stirred for 24 hours under ambient conditions. The reaction mixture was extracted with five 100 ml portions of methylene chloride. The extract was dried over anhydrous magnesium sulfate and evaporated to leave 0.95 grams (22% yield) crude product. Recrystallization from about 50 ml methylene chloride gave 2-amino-3,4,5,6-tetranitrotoluene as yellow crystals (0.60 g), m.p. 183°–185° C. IR (KBr): 3450 and 3330 (NH) and 1620 $cm^{-1}$ ($NO_2$). NMR (($CO_3$)$_2$ CO): δ8.20 (br S, 2, $NH_2$) and 2.45 (S, 3, $CH_3$)

Anal. calcd. for $C_7H_5N_5O_8$: C, 29.26; H, 1.74; N, 24.38. Found: C, 29.25; H, 1.66; N, 24.14.

EXAMPLE 10

1.0 gram of 2-amino-4,6-dinitrotoluene was dissolved in 50 ml of 80% sulfuric acid at room temperature. 1.28 grams of 100% nitric acid was added dropwise with stirring and the reaction mixture was stirred for 24 hours under ambient conditions. The yellow crystalline nitramine 2-amino-N,3,4,5,6-pentanitrotoluene was filtered off at the pump, air-dried, suspended in 50 ml of 96% sulfuric acid and cleaved to the free amine by stirring with 1 ml of anisole for 30 minutes at room temperature. Extraction with five 75 ml portions of methylene chloride was followed by drying over anhydrous magnesium sulfate and evaporation of solvent to give 0.70 grams of 2-amino-3,4,5,6-tetranitrotoluene. The product was recrystallized from about 15 ml of methylene chloride as yellow crystals (0.42 g), m.p. 183°–185° C.

The meta isomer, 3-amino-2,4,5,6-tetranitrotoluene is oxidized to the pentanitrotoluene via the peroxydisulfuric acid oxidation of Example 2. The following examples set forth the necessary procedure to prepare the meta compound.

EXAMPLE 11

2.43 grams of 2,5-dinitro-3-methylbenzoic acid was dissolved in 21.5 grams of oleum (20% $SO_3$, 80% $H_2SO_4$). While the solution is stirred with the temperature maintained at 5°–10° C., 0.84 grams of powdered sodium azide was added cautiously in portions of less than 0.1 g over one hour. Rapid addition of the sodium azide was avoided to prevent any explosion from occurring. Stirring was continued for one hour at 0°–10° C. (gas evolution occurs), 10°–30° C. for two hours and 30°–60° C. for three hours. The resulting dark mixture was then poured over 200 ml of crushed ice to yield a yellow-orange precipitate. The mixture was filtered, washed with water and dried to give 2.02 g of 3-amino-2,5-dinitrotoluene (m.p. 125°–127° C.). Recrystallization from 95% ethanol gave rust colored flakes.

EXAMPLE 12

1 gram of 3-amino-2,5-dinitrotoluene was dissolved in 30 ml of 96% $H_2SO_4$. To this solution, 3 ml of 90% $HNO_3$ was added dropwise and the mixture stirred at room temperature for 3 hours. The mixture was extracted with four 50 ml portions of methylene chloride and the combined extracts dried with anhydrous $MgSO_4$, filtered and evaporated to the nitramine intermediate as a pale yellow oil. The oil was redissolved in 150 ml of 96% $H_2SO_4$. 1 gram of anisole was added and the solution stirred at room temperature for 1 hour. This mixture was extracted with four 100 ml portions of methylene chloride. The combined extracts were again dried with $MgSO_4$, filtered and evaporated. Recrystallization from chloroform gave 665 mg of the meta compound, 3-amino-2,4,5,6-tetranitrotoluene, as a yellow solid (m.p. 192°–193° C.).

The foregoing examples illustrate preferred forms of this invention. It should be apparent to those skilled in the art that parameters of this invention may be varied without departing from the scope of the invention. The specific examples cited should not be considered as limiting the invention in any way and the scope of the invention is to be determined by the scope of the appended claims.

What is claimed is:

1. A process for preparing pentanitrotoluene comprising the steps of:
   preparing an aminodinitrotoluene from a precursor;
   nitrating said aminodinitrotoluene to form a nitramine;
   converting said nitramine to an aminotetranitrotoluene; and
   oxidizing said aminotetranitrotoluene to form pentanitrotoluene.

2. A process for preparing pentanitrotoluene according to claim 1 wherein:
   said precursor is trinitrotoluene.

3. A process for preparing pentanitrotoluene according to claim 2 wherein said aminotetranitrotoluene is 4-amino-2,3,5,6-tetranitrotoluene.

4. A process for preparing pentanitrotoluene according to claim 2 wherein said aminotetranitrotoluene is 2-amino-3,4,5,6-tetranitrotoluene.

5. A process for preparing pentanitrotoluene according to claim 3 wherein:
   said preparation of an aminodinitrotoluene comprises the step of reacting said trinitrotoluene with a solution of $H_2S$ and a catalytic amount of ammonium hydroxide to form 4-amino-2,6-dinitrotoluene;
   said nitration of the aminodinitrotoluene comprises the steps of dissolving said 4-amino-2,6-dinitrotoluene in concentrated $H_2SO_4$ and adding $HNO_3$ to form 4-amino-N,2,3,5,6-pentanitrotoluene;
   said conversion of the nitramine comprises the steps of suspending said 4-amino-N-2,3,5,6-pentanitrotoluene in concentrated $H_2SO_4$ and adding anisole to said suspension to form said 4-amino-2,3,5,6-tetranitrotoluene; and
   said oxidation of the aminotetranitrotoluene comprises the steps of dissolving said 4-amino-2,3,5,6-tetranitrotoluene in oleum to form a solution and adding $H_2O_2$ to said solution.

6. A process for preparing pentanitrotoluene according to claim 3 wherein:
   said prepartion of an aminodinitrotoluene comprises the step of reacting said trinitrotoluene with a solution of $H_2S$ and a catalytic amount of $NH_4OH$ to form 4-amino-2,6-dinitrotoluene;
   said nitration of the aminodinitrotoluene comprises the steps of dissolving said 4-amino-2,6-dinitrotoluene in a mixture of acetic acid and sulfuric acid, adding a mixture of nitric acid and acetic acid to said dissolved 4-amino-2,6-dinitrotoluene to form a reaction mixture, and cooling said reaction mixture with stirring to form 4-amino-N,2,3,6-tetranitrotoluene;
   said conversion of the nitramine comprises the step of dissolving said 4-amino-N,2,3,6-tetranitrotoluene in a mixture of acetic acid and sulfuric acid, adding a mixture of nitric acid and acetic acid to said dissolved 4-amino-N,2,3,6-tetranitrotoluene to form said 4-amino-2,3,5,6-tetranitrotoluene; and
   said oxidation of the aminotetranitrotoluene comprises the steps of dissolving said 4-amino-2,3,5,6-tetranitrotoluene in oleum to form a solution and adding $H_2O_2$ to said solution.

7. A process for preparing pentanitrotoluene according to claim 3 wherein:
   said preparation of the aminodinitrotoluene comprises the step of reacting said trinitrotoluene with a solution of $H_2S$ and a catalytic amount of $NH_4OH$ to form 4-amino-2,6-dinitrotoluene;
   said nitration of the aminodinitrotoluene comprises the steps of adding 4-amino-2,6-dinitrotoluene to nitronium tetrafluoroborate and ethylene dichloride to form a reaction mixture which is then stirred and adding water to said stirred reaction mixture with continued stirring to form 4-amino-N,2,3,6-tetranitrotoluene;
   said conversion of the nitramine comprises the step of dissolving said 4-amino-N,2,3,6-tetranitrotoluene in $H_2SO_4$ to form said 4-amino-2,3,5,6-tetranitrotoluene; and
   said oxidation of the aminotetranitrotoluene comprises the steps of dissolving said 4-amino-2,3,5,6-tetranitrotoluene in oleum to form a solution and adding $H_2O_2$ to said solution.

8. A process for preparing pentanitrotoluene according to claim 3 wherein:
   said preparation of an aminodinitrotoluene comprises the step of reacting said trinitrotoluene with a solution of $H_2S$ and a catalytic amount of $NH_4OH$ to form 4-amino-2,6-dinitrotoluene;
   said nitration of the aminodinitrotoluene comprises the steps of dissolving said 4-amino-2,6-dinitrotoluene in $H_2SO_4$, adding paraformaldehyde to said dissolved 4-amino-2,6-dinitrotoluene to form 4-amino-N-methyl-2,6-dinitrotoluene, and reacting said 4-amino-N-methyl-2,6-dinitrotoluene with a mixture of $HNO_3$ and $H_2SO_4$ to form 4-amino-N,2,3,5,6-pentanitrotoluene;
   said conversion of the nitramine comprises the steps suspending 4-amino-N,2,3,5,6-pentanitrotoluene in concentrated $H_2SO_4$ and adding anisole to said suspension to form said 4-amino-2,3,5,6-tetranitrotoluene; and
   said oxidation of the aminotetranitrotoluene comprises the steps of dissolving said 4-amino-2,3,5,6-tetranitrotoluene in oleum to form a solution and adding $H_2O_2$ to said solution.

9. A process for preparing pentanitrotoluene according to claim 4 wherein:
   said preparation of an aminodinitrotoluene comprises the steps of dissolving said trinitrotoluene in acetic acid to form a solution, slowly adding iron powder to said solution with vigorous stirring, and adding water to form 2-amino-4,6-dinitrotoluene;;
   said nitration of the aminodinitrotoluene comprises the steps of dissolving said 2-amino-4,6-dinitrotoluene in sulfuric acid, adding nitric acid to said dissolved 2-amino-4,6-dinitrotoluene and stirring to form 2-amino-N,3,4,5,6-pentanitrotoluene;
   said conversion of the nitramine comprises the step of suspending said 2-amino-N,3,4,5,6-pentanitrotoluene in sulfuric acid and adding anisole to said suspension to form 2-amino-3,4,5,6-tetranitrotoluene;

said oxidation of the aminotetranitrotoluene comprises the steps of dissolving said 2-amino-3,4,5,6-tetranitrotoluene in oleum to form a solution and adding $H_2O_2$ to said solution.

10. A process for preparing pentanitrotoluene according to claim 1 wherein:

said precursor is 2,5-dinitro-3-methylbenzoic acid.

11. A process for preparing pentanitrotoluene according to claim 10 wherein:

said aminotetranitrotoluene is 3-amino-2,4,5,6-tetranitrotoluene.

12. A process for preparing pentanitrotoluene according to claim 11 wherein:

said preparation of an aminodinitrotoluene comprises the steps of dissolving said 2,5-dinitro-3-methylbenzoic acid in oleum to form a solution, slowly adding sodium azide while cooling and stirring said solution, continued stirring, and recovering 3-amino-2,5-dinitrotoluene as said aminodinitrotoluene;

said nitration of the aminodinitrotoluene comprises the steps of dissolving said 3-amino-2,5-dinitrotoluene in concentrated $H_2SO_4$ and adding $HNO_3$ to form a nitramine intermediate;

said conversion of said nitramine intermediate comprises the steps of suspending said nitramine intermediate in concentrated $H_2SO_4$ and adding anisole to said suspension to form said 3-amino-2,4,5,6-tetranitrotoluene; and said oxidation of the aminotetranitrotoluene comprises the steps of dissolving said 3-amino-2,4,5,6-tetranitrotoluene in oleum to form a solution and adding $H_2O_2$ to said solution.

* * * * *